United States Patent
Jung et al.

(10) Patent No.: US 12,005,447 B2
(45) Date of Patent: Jun. 11, 2024

(54) APPARATUS AND METHOD FOR BIO-PARTICLE DETECTION

(71) Applicant: SAMSUNG ELECTRONICS CO., LTD., Suwon-si (KR)

(72) Inventors: Won Jong Jung, Seoul (KR); Hyeong Seok Jang, Seoul (KR); Kak Namkoong, Seoul (KR); Hyung Jun Youn, Suwon-si (KR); Jae Hong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/889,085

(22) Filed: Aug. 16, 2022

(65) Prior Publication Data
US 2023/0302447 A1 Sep. 28, 2023

(30) Foreign Application Priority Data
Mar. 23, 2022 (KR) ........................ 10-2022-0035899

(51) Int. Cl.
*B01L 7/00* (2006.01)
*B01L 3/00* (2006.01)
(Continued)

(52) U.S. Cl.
CPC ........... *B01L 3/502715* (2013.01); *B01L 7/52* (2013.01); *G01N 15/06* (2013.01);
(Continued)

(58) Field of Classification Search
CPC .............. B01L 3/502715; G01N 15/06; G01N 2015/0065; G01N 2015/03; G01N 2015/0693; G01N 33/48721
See application file for complete search history.

(56) References Cited

U.S. PATENT DOCUMENTS

| D698,938 S | 2/2014 | Fonseca |
| D699,369 S | 2/2014 | Fonseca |

(Continued)

FOREIGN PATENT DOCUMENTS

| CN | 102507395 A | 6/2012 |
| CN | 110927076 A | 3/2020 |

(Continued)

OTHER PUBLICATIONS

You et al., "Ultrafast Photonic PCR Based on Photothermal Nanomaterials," Trends in Biotechnology, June, vol. 38, No. 6, pp. 637-649. (Year: 2020).*

(Continued)

*Primary Examiner* — Young J Kim
(74) *Attorney, Agent, or Firm* — Sughrue Mion, PLLC

(57) ABSTRACT

An apparatus and method for bio-particle detection are provided. The apparatus for bio-particle detection includes: a bio-particle detection chip including a substrate having a plurality of through-hole groups, each through-hole group of the plurality of through-hole groups including through-holes which pass through the substrate from a first surface of the substrate toward an second surface of the substrate opposite to the first surface, and which are configured to accommodate a sample solution loaded therein; and a processor configured to determine a number of through-holes, among the through holes of at least one through-hole group of the plurality of through-hole groups, having a target material encapsulated therein, based on at least one of an electrical signal and an optical signal corresponding to the through-holes of the at least one through-hole group, and to estimate a concentration of the target material based on the determined number.

20 Claims, 15 Drawing Sheets

(51) Int. Cl.
  *G01N 15/06* (2006.01)
  *G01N 15/01* (2024.01)
  *G01N 15/075* (2024.01)
(52) U.S. Cl.
  CPC .............. *B01L 2300/0645* (2013.01); *B01L 2300/0654* (2013.01); *B01L 2300/0681* (2013.01); *B01L 2300/1822* (2013.01); *B01L 2300/1894* (2013.01); *G01N 15/01* (2024.01); *G01N 15/075* (2024.01)

(56) References Cited

U.S. PATENT DOCUMENTS

| | | | |
|---|---|---|---|
| D722,385 S | 2/2015 | Fonseca | |
| D749,234 S | 2/2016 | Fonseca | |
| 9,816,910 B2 | 11/2017 | Bocchi et al. | |
| 9,891,157 B2 | 2/2018 | Bocchi et al. | |
| 9,903,803 B2 | 2/2018 | Smolak et al. | |
| 10,012,579 B2 | 7/2018 | Bocchi et al. | |
| 10,571,475 B2 | 2/2020 | Bocchi et al. | |
| 10,627,420 B2 | 4/2020 | Pallas et al. | |
| 10,627,421 B2 | 4/2020 | Ghenciu et al. | |
| 2004/0043479 A1* | 3/2004 | Briscoe | G01N 30/6095 435/288.5 |
| 2013/0065777 A1 | 3/2013 | Altug et al. | |
| 2015/0044686 A1 | 2/2015 | Pallas et al. | |
| 2015/0045252 A1 | 2/2015 | Maher | |
| 2015/0080247 A1 | 3/2015 | Pallas et al. | |
| 2015/0328634 A1 | 11/2015 | Fonseca | |
| 2019/0241934 A1 | 8/2019 | Maher | |
| 2019/0346358 A1 | 11/2019 | Stakenborg et al. | |
| 2019/0381502 A1* | 12/2019 | Pallas | B01L 3/50 |
| 2020/0319221 A1 | 10/2020 | Ghenciu et al. | |

FOREIGN PATENT DOCUMENTS

| | | |
|---|---|---|
| JP | 2004-184100 A | 7/2004 |
| JP | 2015-511016 A | 4/2015 |
| KR | 10-1433189 B1 | 8/2014 |
| KR | 10-1681179 B1 | 11/2016 |
| KR | 10-1831335 B1 | 2/2018 |
| WO | 2012/072822 A1 | 6/2012 |
| WO | 2012/072823 A1 | 6/2012 |
| WO | 2012/144554 A1 | 10/2012 |

OTHER PUBLICATIONS

Communication dated Jul. 19, 2023, issued by the European Patent Office in European Application No. 22198921.3.
Kang et al., "Graphene Oxide-Supported Microwell Grids for Preparing Cryo-EM Samples with Controlled Ice Thickness", Advanced Materials / vol. 33, Issue 43 / 2102991, Sep. 12, 2021, https://doi.org/10.1002/adma.202102291, (1 page total).
Lippe, "Flow Virometry: a Powerful Tool To Functionally Characterize Viruses", Journal of Virology, American Society for Microbiology, vol. 92, Issue 3, Feb. 2018, (11 pages total).

* cited by examiner

APPARATUS AND METHOD FOR BIO-PARTICLE DETECTION

CROSS-REFERENCE TO RELATED APPLICATION(S)

This application claims priority from Korean Patent Application No. 10-2022-0035899, filed on Mar. 23, 2022, in the Korean Intellectual Property Office, the entire disclosure of which is incorporated by reference herein for all purposes.

BACKGROUND

1. Field

The following description relates to an apparatus and method for bio-particle detection.

2. Description of Related Art

Clinical or environmental samples are analyzed by a series of biochemical, chemical, and mechanical treatment processes. Recently, there has been considerably increasing interest in developing techniques for diagnosis or monitoring of biological samples. Molecular diagnosis based on nucleic acid amplification techniques has excellent accuracy and sensitivity, and thus is increasingly used in various applications, ranging from diagnosis of infectious diseases or cancer to pharmacogenomics, development of new drugs, and other medical therapies. Microfluidic devices are widely used to analyze samples in a simple and accurate manner according to these various purposes.

SUMMARY

According to an aspect of an embodiment, an apparatus for bio-particle detection includes: a bio-particle detection chip including a substrate having a plurality of through-hole groups, each through-hole group of the plurality of through-hole groups including through-holes which pass through the substrate from a first surface of the substrate toward an second surface of the substrate opposite to the first surface, and which are configured to accommodate a sample solution loaded therein; and a processor configured to determine a number of through-holes, among the through holes of at least one through-hole group of the plurality of through-hole groups, having a target material encapsulated therein, based on at least one of an electrical signal and an optical signal corresponding to the through-holes of the at least one through-hole group, and to estimate a concentration of the target material based on the determined number.

The through-holes of each through-hole group of the plurality of through-hole groups may have diameters different than diameters of the through-holes of other through-hole groups of the plurality of through-hole groups.

The diameters of the through-holes in the plurality of through-hole groups may increase in a flow direction of the sample solution.

The apparatus may further include an optical signal detector including: a light source configured to emit light to the bio-particle detection chip; and a detector configured to measure the optical signal scattered or reflected from the bio-particle detection chip.

The processor may be further configured to determine the number of through-holes having the target material encapsulated therein, based on fluorescence measured by the optical signal detector, the fluorescence emanating from the target material by the light emitted to the loaded sample solution.

The processor may be configured to determine the number of through-holes having the target material encapsulated therein, based on transmittance of the light through the through-holes measured by the detector.

The substrate may include a structure formed with a metal nanostructure, and the processor may be further configured to identify a type of the target material based on plasmon resonance measured by the optical signal detector, the plasmon resonance occurring when the target material is attached to the structure formed with the metal nanostructure.

The structure formed with the metal nanostructure may have a metasurface.

The through-holes in the at least one through-hole group of the plurality of through-hole groups may be arranged in a photonic crystal, and the processor may be further configured to determine the number of through-holes having the target material encapsulated therein, based on a spectrum change in the photonic crystal measured by the detector.

The apparatus may further include electrodes or transistors provided in at least a portion of the through-holes of each of the plurality of through-hole groups, and configured to measure an electrical signal corresponding to the at least the portion of the through-holes.

The processor may be further configured to determine the number of through-holes having the target material encapsulated therein, based on at least one of an impedance change and a current change measured by the electrodes or the transistors.

The apparatus may further include a temperature controller configured to control temperature of the through-holes to be at least one of a thermal dissolution temperature, a reverse transcription temperature, and a bio-particle amplification temperature.

In response to the target material being amplified based on temperature controlled by the temperature controller, the processor may be further configured to determine the number of through-holes having the target material encapsulated therein, based on a result of the amplification.

The processor may be further configured to estimate the concentration of the target material based on the determined number of through-holes having the target material encapsulated therein, and a predetermined target material concentration estimation model.

The substrate may include a structure of multiple layers in which the plurality of through-hole groups are formed, and the sample solution flows through channels formed between the respective layers.

The processor may be further configured to determine the number of through-holes having the target material encapsulated therein, based further on photothermal particles labeled on the target material before being loaded into the through-holes.

The apparatus may further include an optical signal detector including: a light source configured to emit light onto the bio-particle detection chip; and a detector configured to measure the optical signal scattered or reflected from the bio-particle detection chip, and the processor may be further configured to determine the number of through-holes having the target material encapsulated therein, based further on the optical signal from the photothermal particles.

The apparatus may further include a temperature measuring sensor configured to measure temperature of the through-holes, and the processor may be further configured to determine the number of through-holes having the target material encapsulated therein, based further on an amount of heat generated by a photothermal effect of the photothermal particles and measured by the temperature measuring sensor.

According to an aspect of an embodiment, an apparatus for bio-particle detection includes: a first main body including a sample solution inlet and a sample solution outlet; a second main body structurally connected to the first main body and configured to allow a fluid to flow; a bio-particle detection chip provided between the first main body and the second main body, the bio-particle detection chip including a substrate having a plurality of through-hole groups, each through-hole group of the plurality of through-hole groups including through-holes which pass through the substrate from a first surface of the substrate toward an second surface of the substrate opposite to the first surface, and which are configured to accommodate a sample solution loaded therein; channels provide between the first main body and the second main body, and configured to have a sample solution flow therethrough; and a processor configured to determine a number of through-holes, among the through holes of at least one through-hole group of the plurality of through-hole groups, having a target material encapsulated therein, based on at least one of an electrical signal and an optical signal corresponding to the through-holes of the at least one through-hole group, and estimate a concentration of the target material based on the determined number.

The through-holes may be configured to be loaded with the sample solution by capillary action.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
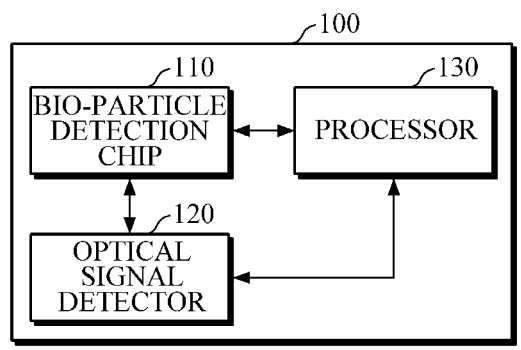
FIG. 1 is a block diagram illustrating an apparatus for bio-particle detection according to an embodiment of the present disclosure.

Embodiments of the disclosure are described in detail below with reference to the accompanying drawings.

Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware, software, or a combination thereof.

Hereinafter, various embodiments of an apparatus and method for bio-particle detection will be described in detail with reference to the accompanying drawings.

FIG. 1 is a block diagram illustrating an apparatus for bio-particle detection according to an embodiment.

Referring to FIG. 1, an apparatus 100 for bio-particle detection may include a bio-particle detection chip 110, an optical signal detector 120, and a processor 130. The optical signal detector 120 may include a light source 121 and a detector 122.

The bio-particle detection chip 110 may include through holes into which a sample solution may be loaded.

The sample solution may be a specimen or a diluted specimen solution. For example, the sample solution may include bio-fluids, including at least one of respiratory secretions, blood, urine, perspiration, tears, saliva, transudate, exudate, and any other liquids produced by the human body, a swab sample of the upper respiratory tract, or a solution of the bio-fluid or the swab sample dispersed in another medium. In this case, the other medium may include water, saline solution, alcohol, phosphate buffered saline solution, vital transport media, and other suitable solvents, but is not limited thereto. A volume of the sample may be in a range of 1 µL to 1000 µL, but is not limited thereto.

The sample solution may contain a target material. In this case, the target material may include ribonucleic acid (RNA), deoxyribonucleic acid (DNA), peptide nucleic acid (PNA), and locked nucleic acid (LNA), a virus (e.g., a duplex of one or more of an RNA virus, a DNA virus, a PNA virus, and aLNA virus), bacteria, pathogen, germ, oligopeptide, protein, toxin, and other organic material, but the target material is not limited thereto.

The sample solution and/or the target material may be pre-treated before being loaded into the through holes. A material or a structure (e.g., storage or functional membrane) for pre-treatment of the sample solution may be provided inside or outside of the apparatus 100 for bio-particle detection. For example, each target material may be subjected to surface treatment. In this case, fluorescence, photothermal particles, quantum dot, or other markers may be labeled on the target material by an antigen-antibody reaction. However, the pre-treatment is not limited thereto.

The bio-particle detection chip 110 may include a plurality of through-hole groups, and the through-holes included in each through-hole group may pass through a substrate from a surface of the substrate toward an opposite surface of the substrate.

In this case, the respective through-hole groups may be different from each other in terms of physical properties (e.g., diameter, volume, shape, and arrangement interval), and/or type or presence of additional components (e.g., optical signal detector, electrical signal measurer, structure having a metal nanostructure, photonic crystal, temperature measurer, and temperature controller) for use in estimating a concentration of the target material.

For example, the through-holes in the respective through-hole groups may have different diameters. In this case, the diameter of the through-holes in the respective through-hole groups may gradually increase in a flow direction of the sample solution. However, the through-holes groups are not limited thereto.

In another example, any one of the plurality of through-hole groups may have a structure formed with a metal nanostructure, and another group includes through-holes having a photonic crystal arrangement by adjusting an arrangement interval between the through-holes, and yet another group may include a temperature sensor and the like for measuring an amount of heat measured by the temperature difference and generated by the photothermal effect of photothermal particles labeled on the target material. In this case, the through-holes in the respective through-hole groups may have the same diameter. Further, the plurality of through-hole groups may have the same characteristics.

In yet another example, the plurality of through-hole groups may be different not only in terms of diameter, but also in terms of type or presence of the additional components for use in estimating a concentration of the target material.

A shape of the bio-particle detection chip 110, in which the plurality of through-hole groups have different diameters, will be described in detail below with reference to FIGS. 2A and 2B.

Figure 2A:
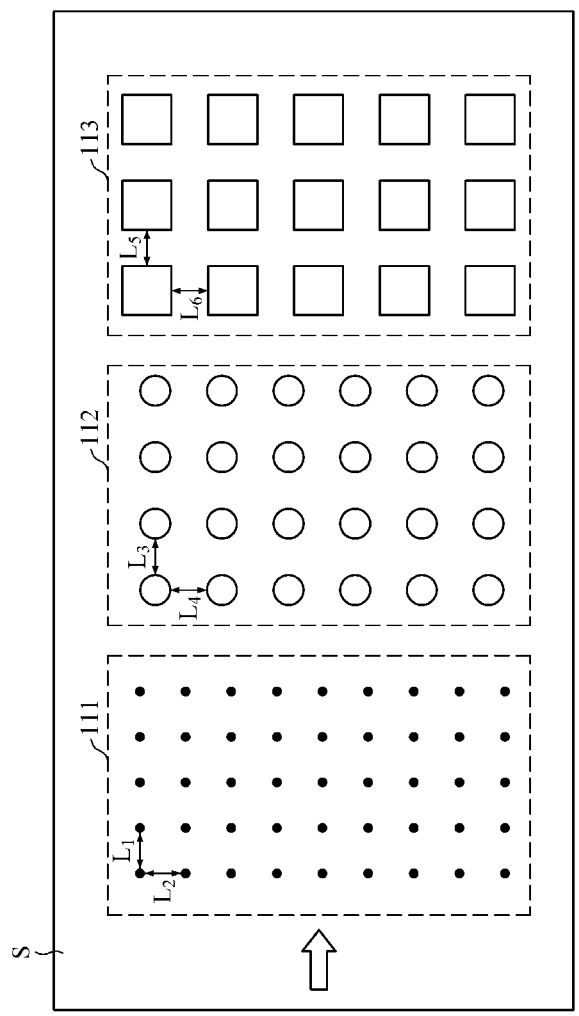
FIGS. 2A and 2B are diagrams illustrating a bio-particle detection chip of FIG. 1 according to an embodiment of the present disclosure.
Figure 2B:
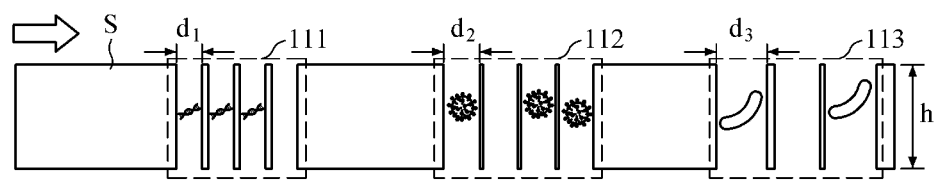

FIGS. 2A and 2B are diagrams illustrating the bio-particle detection chip 110 of FIG. 1 according to an embodiment of the present disclosure.

FIG. 2A is a diagram illustrating a surface of the bio-particle detection chip 110, and FIG. 2B is a diagram illustrating a front surface of the bio-particle detection chip 110.

Referring to FIGS. 2A and 2B, the bio-particle detection chip 110 may include a substrate S, a plurality of through-hole groups, e.g., a first through-hole group 111, a second through-hole group, and a third through-hole group 113.

The substrate S may be made of any one of an inorganic matter, such as silicon (Si), glass, polymer, metal, ceramic, graphite, etc., acrylic material, polyethylene terephthalate (PET), polycarbonate, polystylene, and polypropylene, SixNy, TiO2, and SiO2, but is not limited thereto. In order to adjust optical properties of the substrate S, the substrate S may be treated with gold (Au) or anti-reflection coating.

A height of the substrate S, i.e., a length (h in FIG. 2B) from one surface to the other surface of the substrate S, may be in a range of from 1 μm to 10 μm, but is not limited thereto.

The sample solution may be loaded into the through-holes of at least any one of the first through-hole group 111 to the third through-hole group 113 by flowing in a direction indicated by an arrow (see FIGS. 2A and 2B). In this case, the sample solution may be loaded into the through-holes by capillary action. That is, the sample solution may flow in the direction indicated by the arrow, to be sequentially loaded into the through-hole groups in the order from the first through-hole group 111 to the third through-hole group 113 by capillary action according to elapsed time.

In FIGS. 2A and 2B, the through-hole group 111, the second through-hole group 112, and the third through-hole group 113 are shown as an example of the plurality of through-hole groups.

While FIGS. 2A and 2B illustrate an example in which the bio-particle detection chip 110 includes three through-hole groups 111, 112, and 113, the number of the through-groups is not limited thereto, and may be changed variously for different arrangements. Further, the number of the through-holes included in the respective through-hole groups 111, 112, and 113 is merely an example for convenience of explanation, and the number is not limited thereto. The number of the through-holes included in the respective through-hole groups 111, 112, and 113 may be equal to or different from each other.

Referring to FIG. 2A, distances between the through-holes of the first through-hole group 111 are denoted by $L_1$ and $L_2$, distances between the through-holes of the second through-hole group 112 are denoted by $L_3$ and $L_4$, and distances between the through-holes of the third through-hole group 113 are denoted by $L_5$ and $L_6$. In this case, $L_1$ and $L_2$ may be equal to or different from each other, and the same also applies to $L_3$ and $L_4$, and $L_5$ and $L_6$.

In FIG. 2A, the through-holes of the respective through-hole groups 111, 112, and 113 have an N×N arrangement (e.g., the first through-hole group 111 arranged in 4×9 arrangement, the second through-hole group 112 arranged in 4×6 arrangement, and the third through-hole group 113 arrangement in 3×5 arrangement). As described above, with respect to a direction in which the sample solution flows, the respective through-holes are not arranged in a row which is a one-dimensional arrangement, but are arranged in an N×N arrangement which is a two-dimensional arrangement, such that the sample solution may be loaded into the respective through-holes at a faster speed by capillary action. Accordingly, less time is required for quantifying the target material, such that a bio-particle detection speed may be improved, and the size of the apparatus including bio-particle detection chip 110 may be reduced.

The through-holes in at least any one of the through-hole groups 111, 112, and 113 may be arranged in a photonic crystal.

Taking the first through-hole group 111 as an example, a refractive index of the through-holes, which is filled with air or a liquid (such as a sample solution), is different from a refractive index of the substrate S, such that if the distances $L_1$ and $L_2$ between the through holes included in the first through-hole group 111 have a specific period, materials having different refractive indices are arranged with periods, thereby forming a photonic crystal.

Referring to FIG. 2B, an example is illustrated in which the through-holes of the first through-hole group 111 has a diameter of $d_1$, the through-holes of the second through-hole group 112 has a diameter of $d_2$, and the through-holes of the third through-hole group 111 has a diameter of $d_3$.

The diameters $d_1$, $d_2$, and $d_3$ of the through-holes of the plurality of through-holes groups 111, 112, and 113 may be different from each other.

The diameters $d_1$, $d_2$, and $d_3$ of the through-holes of the plurality of through-holes groups 111, 112, and 113 may be determined based on a size of a target material, of which concentration is to be estimated. In this case, the diameters $d_1$, $d_2$, and $d_3$ of the through-holes may have a size that allows for encapsulation of one corresponding target material.

For example, the diameters of the respective through-hole groups may gradually increase in a flow direction of the sample solution, e.g., a direction indicated by an arrow in FIG. 2B. That is, $d_2$ may be greater than $d_1$, and $d_3$ may be greater than $d_2$, but the diameters are not limited thereto. In this case, the diameter $d_1$ of the through-holes of the first through-hole group may be 10 nm or less, the diameter $d_2$ of the through-holes of the second through-hole group may be, for example, about 100 nm, and the diameter $d_3$ of the through-holes of the third through-hole group may be 1 μm or less, but the diameters of the through-holes of the respective through-hole group are not limited thereto and may be changed variously for different arrangements.

In arrangements with through-holes having sizes as described above, among target materials, DNA and RNA may be encapsulated in the first through-hole group 111; a virus (e.g., DNA virus or RNA virus) may be encapsulated in the second through-hole group 112; and bacteria may be encapsulated in the third through-hole group 113.

If the diameter $d_1$ of the first through-hole group 111 is, e.g., 5 nm, the diameter $d_2$ of the second through-hole group is, e.g., 100 nm, and the diameter $d_3$ of the third through-hole group 113 is, e.g., 1 μm, bacteria used herein as an example generally have a size greater than or equal to 0.5 μm, such that the bacteria may not be encapsulated in the first through-hole group 111 or the second through-hole group 112, but may be encapsulated in the third through-hole group 113.

As described above, the diameters of the respective through-hole groups have different sizes, such that target materials may be automatically encapsulated in through-holes of the respective through-hole groups that fit the sizes of the target materials. In this case, if the sample solution contains two or more target materials, e.g., both virus and bacteria, the virus may be encapsulated (e.g., in through-holes of the second through-hole group 112), and the bacteria may be encapsulated (e.g., in through-holes of the third through-hole group 113). Accordingly, by automatically classifying the target materials according to their sizes, convenience and accuracy in estimating the concentration of target materials may be improved.

However, the present disclosure is not limited thereto, and the diameters $d_1$, $d_2$, and $d_3$ of the through-holes of the plurality of through-holes groups may be equal to each other, as illustrated above in FIG. 1.

The substrate S of the bio-particle detection chip 110 may be formed in a multi-layer structure. A shape of the substrate S formed in a multi-layer structure will be described below with reference to FIG. 3.

Figure 3:
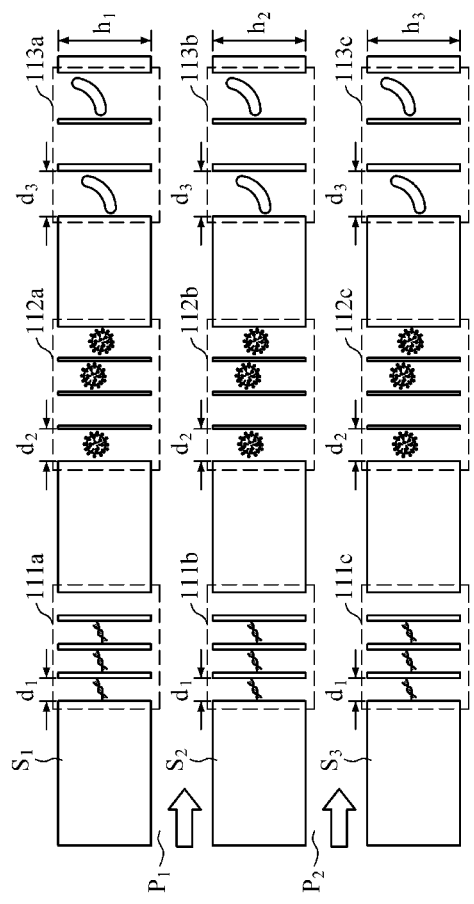
FIG. 3 is a diagram illustrating a bio-particle detection chip formed in a multi-layer structure according to an embodiment of the present disclosure.

FIG. 3 is a diagram illustrating a bio-particle detection chip formed in a multi-layer structure according to an embodiment of the present disclosure. Referring to FIG. 3, the bio-particle detection chip according to an embodiment of the present disclosure may include a first substrate $S_1$, a second substrate $S_2$, and a third substrate $S_3$. While FIG. 3 illustrates the bio-particle detection chip formed in a three-layer structure, the number of layers of the bio-particle detection chip is not limited thereto and may be changed for different arrangements.

In FIG. 3, an example is illustrated in which the first substrate $S_1$ has a height of $h_1$, the second substrate $S_2$ has a height of $h_2$, and the third substrate $S_3$ has a height of $h_3$. In this case, $h_1$ may be in a range of from 1 μm to 10 μm, but is not limited thereto, and $h_1$ and $h_3$ may be equal to or different from each other.

The plurality of through-hole groups may be formed in each layer. For example, the first substrate $S_1$ may include through-hole groups 111a, 112a, and 113a, the second substrate $S_2$ may include through-hole groups 111b, 112b, and 113b, and the third substrate $S_3$ may include through-hole groups 111c, 112c, and 113c.

The sample solution may flow through channels, formed between the respective layers, in directions indicated by the two arrows as seen in FIG. 3 (i.e., a channel $P_1$ formed between the first substrate $S_1$ and the second substrate $S_2$, a channel $P_2$ formed between the second substrate $S_2$ and the third substrate $S_3$), to be loaded into the through-holes of the respective through-hole groups 111a to 113a, 111b to 113b, and 111c to 113c. In this case, the sample solution may be loaded into the through-holes of the respective through-hole groups by capillary action.

As the bio-particle detection chip is formed in a three-dimensional multi-layer structure, as illustrated in FIG. 3, the sample solution may be loaded into the respective through-holes at a faster speed by capillary action. Accordingly, less time is required for quantifying the target material, such that a bio-particle detection speed may be improved, and the size of the apparatus including bio-particle detection chip 110 may be reduced.

Referring back to FIG. 1, the optical signal detector 120 may include a light source for emitting light onto the bioparticle detection chip 110, and a detector for measuring an optical signal scattered or reflected from the bio-particle detection chip 110.

The light source may emit light onto the through-holes of the bio-particle detection chip 110, the sample solution loaded into the through-holes, a structure (not shown) formed with a metal nanostructure, and the like. The light source may include an LED, laser, or a vertical-cavity surface-emitting laser, but is not limited thereto. In addition, light emitted by the light source may be light in various wavelength ranges. For example, the light source may emit light having wavelengths ranging from ultraviolet (UV) to infrared (IR), but is not limited thereto.

The detector may measure an optical signal scattered or reflected from the bio-particle detection chip 110. The detector may include a photomultiplier tube, a photo detector, a photomultiplier tube array, a photo detector array, or a complementary metal-oxide semiconductor (CMOS) image sensor, but is not limited thereto.

The optical signal may include fluorescence, phosphor, absorbance, surface plasmon resonance, or any other suitable markers.

The detector may measure, for example, fluorescence emanating from the target material after light is emitted onto the sample solution loaded into the through-holes, light transmittance at the through-holes, plasmon resonance occurring when the target material is attached to the structure (not shown) having the metal nanostructure, a spectrum change in photonic crystal if the through-holes has a photonic crystal arrangement, and the like. However, the detector is not limited thereto. In this case, a relatively low-power detector may be used to measure the spectrum change in photonic crystal.

The optical signal detector 120 may include a filter for passing light of a specific wavelength, a mirror for directing the light emanating from the target material toward the detector, and a lens for collecting light emanating from the target material.

The processor 130 may estimate a concentration of the target material based on the optical signal measured by the optical signal detector 120 and scattered or reflected from the bio-particle detection chip 110.

The processor 130 may estimate the concentration of the target material for each through-hole group. In the case where the sample solution contains a plurality of target materials, the processor 130 may estimate the concentration of each target material for each through-hole group in which different target materials are encapsulated.

In this case, the processor 130 may estimate the centration of the target material by using an optical signal from all the through-holes of a specific through-hole group (e.g., the first through-hole group) of the bio-particle detection chip 110. Alternatively, by using only an optical signal from some of the through-holes of the first through-hole group, the processor 130 may estimate an optical signal of all the through-holes of the first through-hole group to estimate the concentration of the target material.

The processor 130 may determine the number of through-holes, in which the target material is encapsulated, based on the measured optical signal, and may estimate the concentration of the target material based on the determined number.

For example, the processor 130 may determine the number of through-holes, in which the target material is encapsulated, based on fluorescence emanating from the target material.

That is, in the above pre-treatment process (e.g., a process in which the target material is conjugated with fluorescence in an antigen-antibody reaction) a characteristic fluorescence signal may be generated by the light emitted by the optical signal detector 120. If the characteristic fluorescence signal is measured by the optical signal detector 120 for a predetermined period of time, the processor 130 may determine the number of through-holes having the target material encapsulated therein, in which the number corresponds to a numerical value of the measured fluorescence signal, by using, e.g., a predetermined equation or algorithm. However, the determination is not limited to the above example.

In another example, the processor 130 may determine the number of through-holes, having the target material encapsulated therein, based on light transmittance at the through-holes. That is, based on whether the target material is encapsulated or not, a level of light transmission through the respective through-holes, after being emitted by the optical signal detector 120, and light reflectance may vary, and the absorbance may be measured by the optical signal detector 120 as described above.

In this case, the processor 130 may determine the number of through-holes, having the target material encapsulated therein, in such a manner that among the respective through-holes, if light transmittance of through-holes is greater than or equal to a predetermined threshold value, the processor 130 may determine that the target material is encapsulated in the through-holes; by contrast, if light transmittance of through-holes is less than the predetermined threshold value, the processor 130 may determine that the target material is not encapsulated in the through-holes.

Alternatively, rather than using the light transmittance of the respective through-holes, by using only light transmittance of the entire specific through-hole group, e.g., the entire first through-hole group, the processor 130 may estimate a concentration of the target material. In this case, the processor 130 may determine the number of through-holes having the target material encapsulated therein, in which the number corresponds to the measured light transmittance of the entire first through-hole group, by using a predetermined equation and the like. However, the determination is not limited thereto.

In another example, based on a spectrum change in photonic crystal formed on the bio-particle detection chip 110, the processor 130 may determine the number of through-holes having the target material encapsulated therein, which will be described in detail below with reference to FIG. 4.

Figure 4:
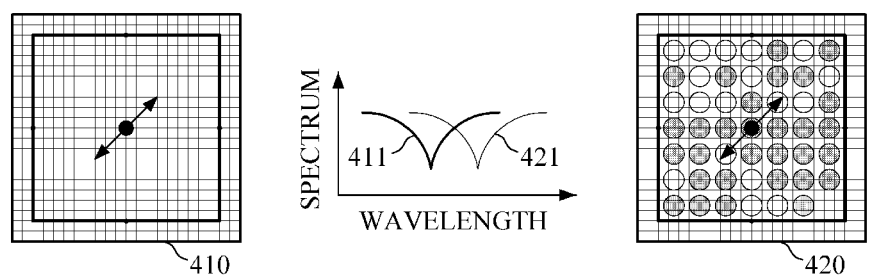
FIG. 4 is a diagram explaining a process of determining the number of through-holes, having a target material encapsulated therein, based on a photonic crystal according to an embodiment of the present disclosure.

FIG. 4 is a diagram explaining a process of determining the number of through-holes, having a target material encapsulated therein, based on a photonic crystal according to an embodiment of the present disclosure.

As illustrated above in FIG. 2A, through-holes included in at least one of the through-hole groups of the bio-particle detection chip may be arranged in a photonic crystal. Based on a spectrum change in photonic crystal, which is formed when materials having different refractive indices are arranged with periods, the processor 130 may determine the number of through-holes having the target material encapsulated therein.

Referring to FIG. 4, reference numerals 410 and 420 denote the through-holes arranged in a photonic crystal; reference numerals 411 and 421 denote a spectrum in the photonic crystal; reference numerals 410 and 411 denote a case where the target material is not encapsulated in the through-holes; and reference numerals 420 and 421 denote a case where target material is encapsulated in the through-holes.

As illustrated in FIG. 4, a spectrum measured in a case 421 where the target material is encapsulated in the through-holes arranged in a photonic crystal, is different from a spectrum measured in a case 411 where the target material is not encapsulated therein.

The processor 130 may calculate a difference between the spectrum 411, measured in the case where the target material is not encapsulated, and the spectrum 421 measured in the case where the target material is encapsulated, and based on the calculated difference, the processor 130 may determine the number of through-holes having the target material encapsulated therein.

For example, the processor 130 may extract a valley point, a peak point, or a wavelength difference between valley points, and other measured/calculated values of the spectrum as features, and may determine the number of through-holes, having the target material encapsulated therein, by using the extracted features, a predetermined equation, and the like. However, the determination is not limited to the above example.

Referring back to FIG. 1, the bio-particle detection chip 110 may include a structure formed with a metal nanostructure. In this case, the processor 130 may identify the type of target material or may estimate the concentration of the target material based on an optical signal generated in the structure having the metal nanostructure, which will be described in detail below with reference to FIGS. 5A to 5C.

Figure 5A:
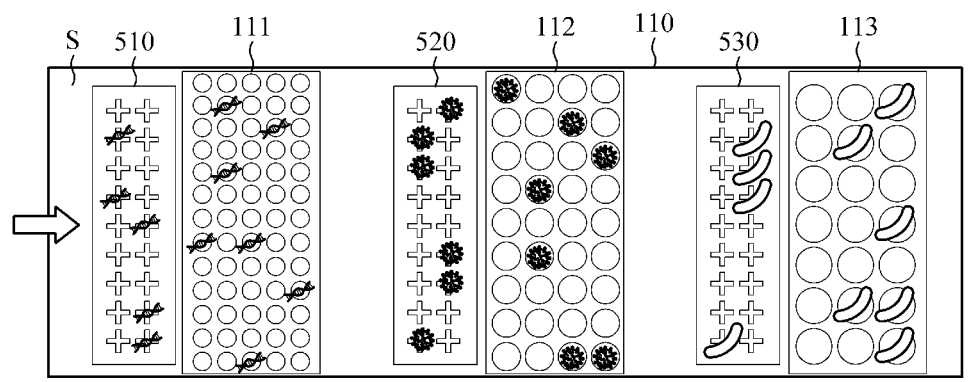
FIGS. 5A and 5B are diagrams illustrating a bio-particle detection chip including structures formed with a metal nanostructure according to an embodiment of the present disclosure.
Figure 5B:
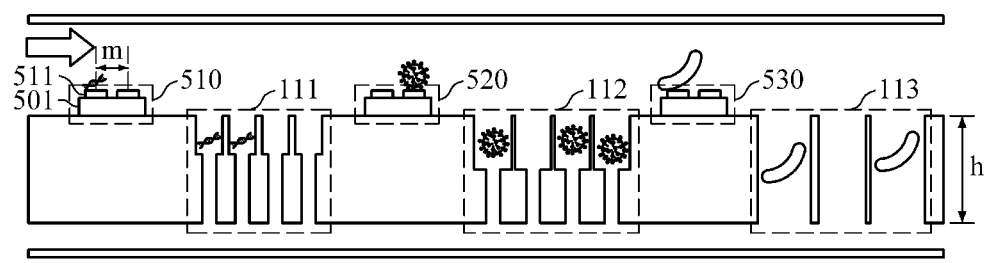

FIGS. 5A and 5B are diagrams illustrating a bio-particle detection chip including structures formed with a metal nanostructure according to an embodiment of the present disclosure.

Referring to FIGS. 5A and 5B, the bio-particle detection chip may include a substrate S, a plurality of through-hole groups 111, 112, and 113, and structures 510, 520, and 530 having a metal nanostructure corresponding to the respective through-hole groups.

For example, as illustrated in FIG. 5B, the structures having the metal nanostructure may be formed such that metal bodies 511 are spaced apart at predetermined intervals on a substrate 501 made of a non-metal material; or in another example, the substrate 501 is made of metal, and has nano-grooves spaced apart at predetermined intervals. However, the arrangement is not limited thereto.

For convenience of explanation, the following description will be given of an example in which the structures having the metal nanostructure are formed such that the metal bodies 511 are spaced apart at predetermined intervals on the substrate 501 made of a non-metal material.

While FIGS. 5A and 5B illustrate an example in which all the through-hole groups 111, 112, and 113 include the structures 510, 520, and 530 having the metal nanostructure, the through-hole groups are not limited thereto, and some of the through-holes may not include the structures having the metal nanostructure.

In FIGS. 5A and 5B, the structures 510, 520, and 530 having the metal nanostructure are located on the left side of the respective through-hole groups 111, 112, and 113 in a flow direction of the sample solution which is indicated by an arrow. However, the structures 510, 520, and 530 having the metal nanostructure are not limited thereto and may be located on one side, the other side, or the right side of the respective through-hole groups 111, 112, and 113.

In addition, unlike the example illustrated in FIGS. 5A and 5B, the structures 510, 520, and 530 having the metal nanostructure may be disposed continuously at a predetermined position (e.g., position indicated by reference numeral 510), without being spaced apart on each of the corresponding through-hole groups 111, 112, and 113.

In some arrangements, the structures having the metal nanostructure may have a metasurface.

Referring to FIG. 5B, the metal bodies 511 of the structure 510 having the metal nanostructure may be spaced apart from each other at predetermined intervals m. That is, a refractive index of the metal bodies 511 is different from a refractive index of the metal bodies 511 filled with air or a liquid such as a sample solution and the like, such that if the distances m between the metal bodies have a predetermined period, materials having different refractive indices are arranged with periods, thereby forming a metasurface.

The metal bodies 511 of each of the structures 510, 520, and 530 having the metal nanostructure may be coated differently for each of the corresponding through-hole groups 111, 112, and 113, i.e., for each target material to be encapsulated in the corresponding through-hole groups 111, 112, and 113. In this case, the type of coating may be formed in advance according to a target material to be estimated. In order to facilitate attachment of the target material, antigen-antibody treatment and/or aptamer treatment may be performed on the structures 510, 520, and 530 having the metal nanostructure.

When the sample solution containing the target material passes through the structures 510, 520, and 530 having the metal nanostructure, such that a portion of the target material is attached to the structures 510, 520, and 530 having the metal nanostructure, the processor 130 may identify the type of target material based on an optical signal measured from the structures 510, 520, and 530 having the metal nanostructure. In this case, the optical signal may be measured by the optical signal detector 120, and may be, for example, plasmon resonance, which will be described in detail below with reference to FIG. 5C.

Figure 5C:
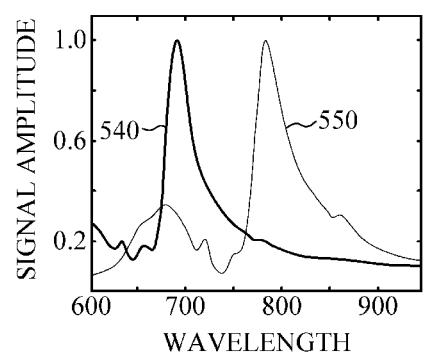
FIG. 5C is a diagram explaining a process of identifying the type of target material by using a metal nanostructure according to an embodiment of the present disclosure.

FIG. 5C is a diagram explaining a process of identifying the type of target material by using a metal nanostructure according to an embodiment of the present disclosure.

FIG. 5C illustrates a reference optical signal 540, which is measured in the case where the bio-particle detection chip does not include the structures having the metal nanostructure, and an optical signal 550 which is measured in the case where the target material is attached to the structures having the metal nanostructure. In this case, the reference optical signal 540 may be received from an external device or may be predefined through a separate process.

When the target material corresponding to the coating of the metal bodies 511 (see FIG. 5B) is attached to the structures having the metal nanostructure, a unique optical signal 550 is generated by localized surface plasmonic resonance (LSPR). That is, in the unique optical signal 550, a transmitted wavelength range is moved compared to the reference optical signal 540.

The processor 130 may identify the type of target material (e.g., DNA, RNA, virus, or bacteria) based on whether there is a difference between the unique optical signal 550 and the reference optical signal 540, ad/or a degree of the difference.

The processor 130 may calculate a degree of difference between the unique optical signal 550 and the reference optical signal 540, and may determine the number of through-holes, having the target material encapsulated therein, based on the calculated degree of difference. For example, the processor 130 may determine the number of through-holes having the target material encapsulated therein, in which the number corresponds to the calculated degree of difference, by using a predetermined equation and the like. However, the determination is not limited thereto.

Referring back to FIG. 1, upon determining the number of through-holes having the target material encapsulated therein, the processor 130 may estimate the concentration of the target material based on a predetermined target material concentration estimation model.

In this case, the processor 130 may estimate the concentration of the target material for each of the through-hole groups.

For example, the processor 130 may estimate the concentration of the target material based on Poisson distribution as represented by the following Equation 1, but is not limited thereto.

$$C = \frac{n}{V_d} = \frac{-\ln(E)}{V_d} \quad \text{[Equation 1]}$$

$$n = -\ln(E)$$

Herein, C denotes the concentration of the target material to be estimated; n denotes the number of through-holes having the target material encapsulated therein, compared to the total number of through-holes of a specific through-hole group (e.g., the first through-hole group); $V_d$ denotes the volume of one through-hole of the first through-hole group; and E denotes a percentage of empty through-holes in the first through-hole group.

Figure 6A:
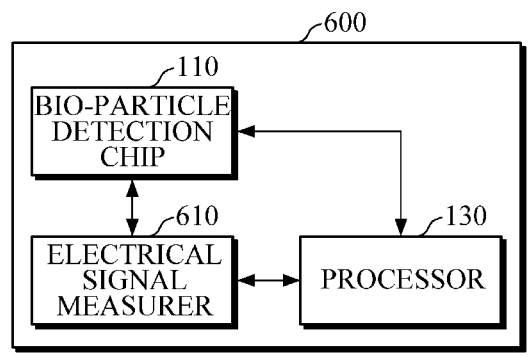
FIG. 6A is a block diagram illustrating an apparatus for bio-particle detection according to another embodiment of the present disclosure.
Figure 6B:
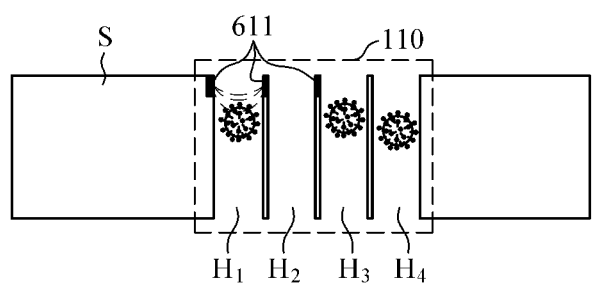
FIG. 6B is a diagram illustrating a shape of a bio-particle detection chip including an electrical signal measurer according to another embodiment of the present disclosure.

FIG. 6A is a block diagram illustrating an apparatus for bio-particle detection according to another embodiment of the present disclosure. FIG. 6B is a diagram illustrating a shape of the bio-particle detection chip 110 including an electrical signal measurer 610 according to another embodiment of the present disclosure.

Referring to FIG. 6A, an apparatus 600 for bio-particle detection may include a bio-particle detection chip 110, the processor 130, and the electrical signal measurer 610. A redundant description thereof will be omitted, and the following description will be focused on the electrical signal measurer 610.

The electrical signal measurer 610 may include electrodes, a transistor array, and a switching matrix for controlling electrical signals of the respective through-holes. In this case, the transistor may include a gate and a source drain.

The electrical signal measurer 610 may be formed in the bio-particle detection chip 110. For example, the electrical signal measurer 610 may be formed in at least one of the plurality of through-hole groups of the bio-particle detection chip 110. In this case, the electrical signal measurer 610 may be formed in the entire or a portion of the through-holes included in a specific through-hole group.

FIG. 6B illustrates the substrate S, the first through-hole group 110 as an example of the through-hole groups, through-holes $H_1$ to $H_4$ included in the first through-hole group 110, and electrodes 611 as an example of the electrical signal measurer 610.

While the electrodes 611 are formed in an upper region of the through-holes $H_1$ and $H_2$ in FIG. 6B, the electrodes 611 are not limited thereto and may be formed in a lower region of the through holes $H_1$ and $H_2$.

For convenience of explanation, FIG. 6B illustrates an example in which the electrodes 611 are formed in only two through holes $H_1$ and $H_2$ among the plurality of through-holes $H_1$ to $H_4$ included in the first through-hole group 110. However, a percentage of the formed electrodes 611 is not limited thereto, and may be formed in all the plurality of through-holes $H_1$ to $H_4$ included in the first through-hole group 110 as described above, or may be formed at a different percentage from the example of FIG. 6B.

When the target material passes through the electrodes 611 formed in the through-holes to be encapsulated in the through-holes, a current, impedance and the like measured in the electrodes 611 is changed. The processor 130 may determine the number of through-holes, having the target material encapsulated therein, based on a change in the measured current and impedance and the like by using surface properties of the target material.

If the change in the impedance or current, which is measured at the electrodes 611, is greater than or equal to a threshold value, the processor 130 may determine that the target material is encapsulated in the through hole $H_1$. By contrast, if the change in impedance or current is not measured, or of the change value is less than the threshold value, the processor 130 may determine that the target material is not encapsulated in the through-hole $H_2$.

In this manner, the processor 130 may determine the number of through-holes (e.g., one in FIG. 6B), in which the target material is encapsulated, compared to the number of the through-holes (e.g., two in FIG. 6B) in which the electrodes are formed.

Then, the processor 130 may estimate the concentration of the target material based on a predetermined target material concentration estimation model and the like.

The apparatus 600 for bio-particle detection may further include an optical signal detector similar to that shown in FIG. 1. In this case, the processor 130 may determine the number of through-holes, having the target material encapsulated herein, by combining the electrical signal measured by the electrical signal measurer 610 with the optical signal measured by the optical signal detector.

Figure 7:
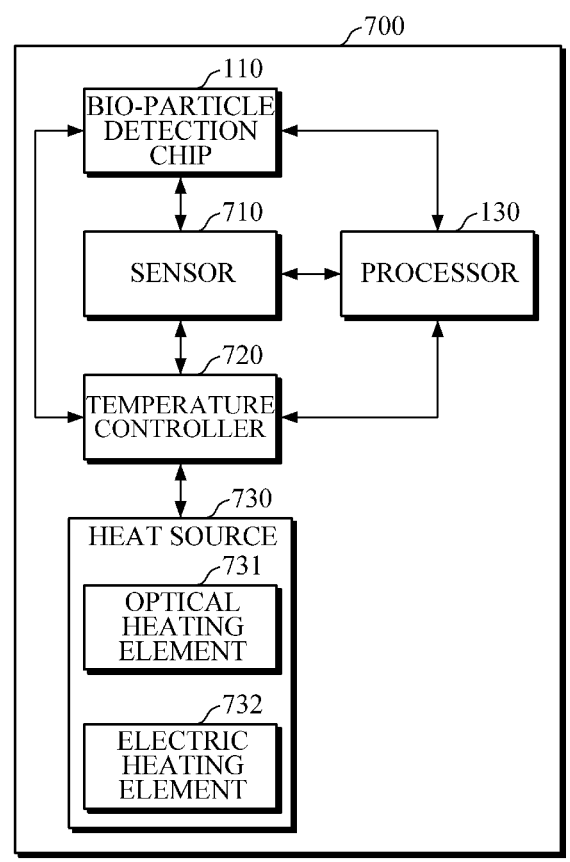
FIG. 7 is a block diagram illustrating an apparatus for bio-particle detection according to yet another embodiment of the present disclosure.

FIG. 7 is a block diagram illustrating an apparatus for bio-particle detection according to yet another embodiment of the present disclosure. Referring to FIG. 7, an apparatus 700 for bio-particle detection may include the bio-particle detection chip 110, the processor 130, a sensor 710, a temperature controller 20, and a heat source 730.

In this case, the sensor 710 may refer to the optical signal detector 120 of FIG. 1 and/or the electrical signal measurer 610 of FIG. 6A. A redundant description thereof will be omitted, and the following description will be focused on the temperature controller 720 and the heat source 730.

The temperature controller 720 may control the temperature of the apparatus 700 for bio-particle detection. For example, the temperature controller 720 may control the temperature of a sample solution, injected into the apparatus 700 for bio-particle detection, to be maintained at an isothermal temperature of 95° C. or higher, or may control temperature of the respective through-holes, formed in the bio-particle detection chip 110, to be maintained within a predetermined temperature range.

The temperature controller 720 may control temperature by using the heat source 730 disposed inside or outside of the apparatus 700 for bio-particle detection. In this case, the heat source 730 may include at least one of an optical heating element 731 and an electric heating element 732, but is not limited thereto.

The optical heating element 731 may include a material for generating heat by using received light. The optical heating element 731 may include, for example, a photothermal film. In this case, the photothermal film may be disposed on one surface or the other surface of the substrate on bio-particle detection chip 110, and a partition wall of the respective through holes. The photothermal film may be formed as a metal layer, but is not limited thereto, and may be made of a metal oxide material, metalloid, and base metal. For example, the photothermal film may be formed as nanoparticles having a size of 50 nm or less in diameter and 50 nm or less in thickness, nanorod, nanodisc, or nanoisland, but is not limited thereto, and may be formed in various nanostructures.

The electrical heating element 732 may include a Peltier element having electrothermal properties, but is not limited thereto.

The temperature controller 720 may control temperature of at least one of the through-hole groups of the bio-particle detection chip 110 to be a thermal dissolution temperature, a reverse transcription temperature, a bio-particle amplification temperature, and the like according to elapsed time.

In this case, the temperature controller 720 may control the temperature of the through-holes according to the type of target material encapsulated in the respective through-hole groups.

For example, in the case where a virus (e.g., DNA virus or RNA virus) is encapsulated in the second through-hole group, the temperature controller 720 may control the temperature of the second through-hole group to be the thermal dissolution temperature. In this case, the viral membrane may be removed by thermal dissolution, such that DNA and RNA as genetic materials may be released. Then, the temperature controller 720 may control the temperature of the second through-hole group to be the reverse transcription temperature or the bio-particle amplification temperature, so as to amplify the target material.

In another example, in the case where the RNA is encapsulated in the first through-hole group of the bio-particle detection chip 110, the temperature controller 720 may control the temperature of the first through-hole group to be the reverse transcription temperature. In this case, the RNA may be reverse transcribed to DNA by reverse transcription.

In yet another example, in the case where the DNA is encapsulated in the first through-hole group of the bio-particle detection chip 110, the temperature controller 720 may control the temperature of the first through-hole group to be the bio-particle amplification temperature. In this case, the bio-particle amplification reaction may include at least one of polymerase chain reaction (PCR) amplification and isothermal amplification, but is not limited thereto. In the case where the bio-particle amplification reaction is the PCR amplification, the temperature controller 720 may control the temperature of the through-holes based on thermal cycling; and in the case where the bio-particle amplification reaction is the isothermal amplification, the temperature controller 720 may control the temperature of the through-holes to be maintained at a specific temperature.

Subsequently, the sensor 710 and/or the processor 130 may determine the number of through-holes, having the target material encapsulated therein, based on a target material amplification result from temperature control by the temperature controller 720.

As illustrated in FIGS. 1 and 6A, the processor 130 may determine the number of through-holes, having the target material encapsulated therein, based on fluorescence emanating from the target material, light transmittance at the through-holes, a spectrum change in photonic crystal, an impedance change, and a current change.

Compared to the case where the target material is not amplified, in the case where the target material is amplified, the sensor 710 may easily measure the fluorescence emanating from the target material, the light transmittance or reflectance at the through-holes, the spectrum change in photonic crystal, the impedance change, and the current change, and thus the processor 130 may determine the number of through-holes having the target material encapsulated therein more accurately.

Based on the determined number of through-holes, the processor 130 may estimate the concentration of the target material as illustrated in FIGS. 1 and 6.

When the target material is amplified, the target material is amplified in the through-holes in which the target material is already encapsulated, and the amplified target material does not leak to the outside of the through-holes. Accordingly, the processor 130 estimates the concentration of the target material based on the number of through-holes having the target material encapsulated therein, in which the concentration of the target material may be the same before/after the amplification of the target material.

Figure 8:
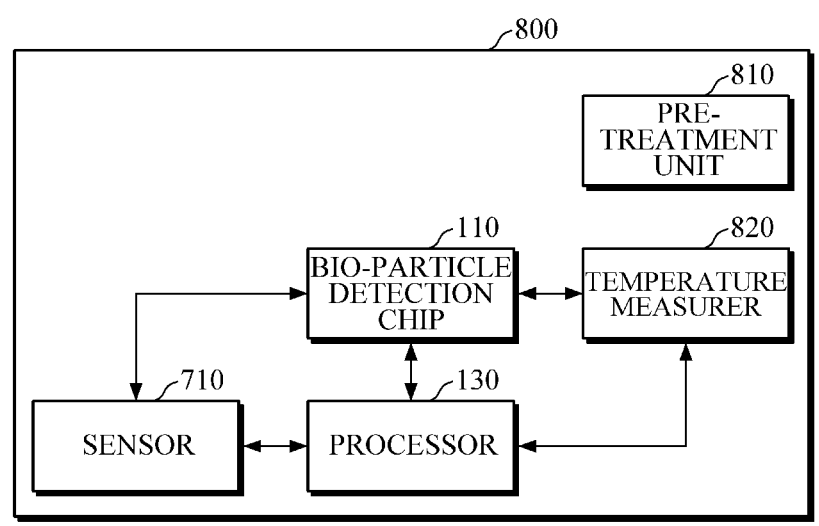
FIG. 8 is a block diagram illustrating an apparatus for bio-particle detection according to still another embodiment of the present disclosure.

FIG. 8 is a block diagram illustrating an apparatus for bio-particle detection according to still another embodiment of the present disclosure. Referring to FIG. 8, an apparatus 800 for bio-particle detection may include the bio-particle detection chip 110, the processor 130, the sensor 710, a pre-treatment unit 810, and a temperature measurer 820.

As in the embodiment of FIG. 7, the sensor 710 may refer to the optical signal detector of FIG. 1 and/or the electrical signal measurer 610 of FIG. 6A.

The pre-treatment unit 810 may perform a pre-treatment process before the sample solution and/or the target material is loaded into the through-holes. The pre-treatment unit 810 may be provided inside or outside of the apparatus 800 for bio-particle detection, and may include a material or a structure (e.g., storage, functional membrane) for pre-treatment.

For example, the pre-treatment unit 810 may perform surface treatment on each target material. In this case, a surface treatment process of each target material may include labeling of photothermal particles, fluorescence, quantum dot, and other markers on each target material by an antigen-antibody reaction.

In another example, the pre-treatment unit 810 may perform heating, chemical treatment, treatment with magnetic beads, solid phase extraction, and treatment with ultrasonic waves on the sample solution.

In yet another example, the pre-treatment unit 810 may mix the sample solution with reverse transcriptase, polymerase, ligase, peroxidase, primer, probe, and the like. In this case, the probe may include oligonucleotide, for example, target specific single strand oligonucleotide, a fluorescent material, quencher, etc., but is not limited thereto.

The photothermal particles labeled on the target material by the pre-treatment process may receive light from the light source of the optical signal detector included in the sensor 710, and may generate heat by photonic heating using the received light.

The photothermal particles may be metal nanoparticles, but are not limited thereto, and may be made of metal oxide material, metalloid, and base metal. In addition, the photothermal particles may further contain carbon black, visible light dye, ultraviolet dye, infrared dye, fluorescent dye, radiation-polarizing dye, pigment, metallic compound, and another suitable absorber material as a photothermal conversion material.

The temperature measurer 820 may measure the temperature of the bio-particle detection chip 110.

When the photothermal particles labeled on the target material receive light from and generate heat by photonic heating, the temperature measurer 820 may measure a temperature change due to the heating from the photothermal particles.

The temperature measurer 820 may measure the temperature of at least any one of the plurality of through-hole groups of the bio-particle detection chip 110. In this case, the temperature measurer 820 may measure the temperature of, for example, the entire first through-hole group or may measure the temperature of some through-holes included in the first through-hole group.

The temperature measurer 820 may include a temperature sensor provided inside or outside of the bio-particle detection chip 110. In this case, the temperature sensor may include a thermocouple having a bimetal junction generating temperature-dependent EMF, a resistive thermometer including materials having electrical resistance proportional to temperature, thermistors, an IC temperature sensor, a quartz thermometer, but is not limited thereto.

Based further on the photothermal particles labeled on the target material by the pre-treatment unit 810, the processor 130 may determine the number of through-holes in which the target material is encapsulated.

For example, the processor 130 may determine the number of through-holes, in which the target material is encapsulate, based on an optical signal from the photothermal particles, e.g., metal nanoparticles.

For example, the processor 130 may extract features from surface-enhanced Raman scattering (SERS) or Raman scattering in metal nanoparticles measured by the optical signal detector, and may determine the number of through-holes having the target material encapsulated therein, in which the number corresponds to the measured optical signal, by using, for example, the extracted features and a predetermined equation. However, the present disclosure is not limited thereto.

In another example, the processor 130 may determine the number of through-holes, having the target material encapsulated therein, based on a temperature change due to a photothermal effect of the metal nanoparticles, and/or an amount of generated heat.

For example, the processor 130 may determine the number of through-holes, having the target temperature encapsulated therein, by using the amount of heat generated in a specific through-hole group, e.g., the entire first through-hole group. In this case, the processor 130 may determine the number of through-holes having the target material encapsulated therein, in which the number corresponds to the measured amount of heat generated in the entire first through-hole group, by using a predetermined equation and the like. However, the present disclosure is not limited thereto.

Alternatively or additionally, the processor 130 may determine the number of through-holes, having the target material encapsulated therein, based on the measured amount of heat generated in some of the through-holes of a specific through-hole group. In this case, the processor 130 may determine the number of through-holes, having the target material encapsulated therein, in such a manner that if the amount of heat generated in through-holes is greater than or equal to a predetermined threshold value, the processor 130 may determine that the target material is encapsulated in the through-holes; by contrast, if the amount of heat generated in through-holes is less than the predetermined threshold value, the processor 130 may determine that the target material is not encapsulated in the through-holes.

Then, the processor 130 may estimate the concentration of the target material in the same manner as in FIG. 1.

Figure 9A:
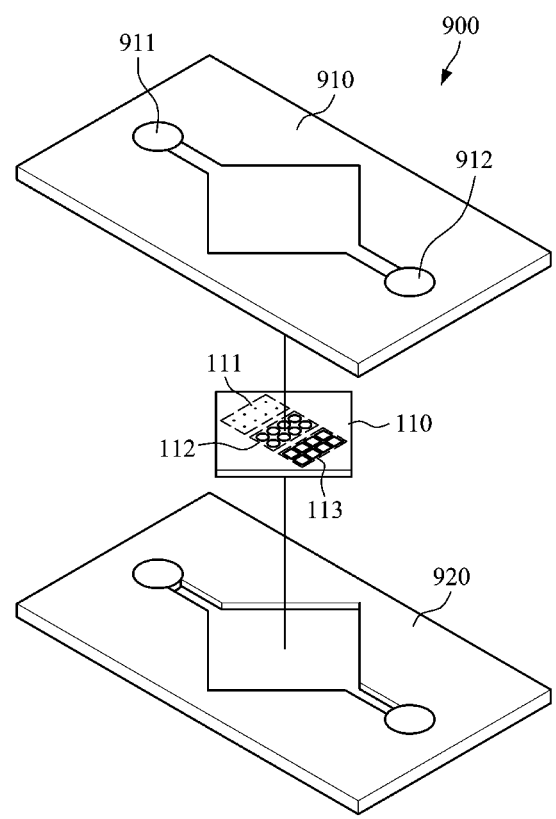
FIG. 9A is an exploded perspective view of an apparatus for bio-particle detection according to an embodiment of the present disclosure.
Figure 9B:
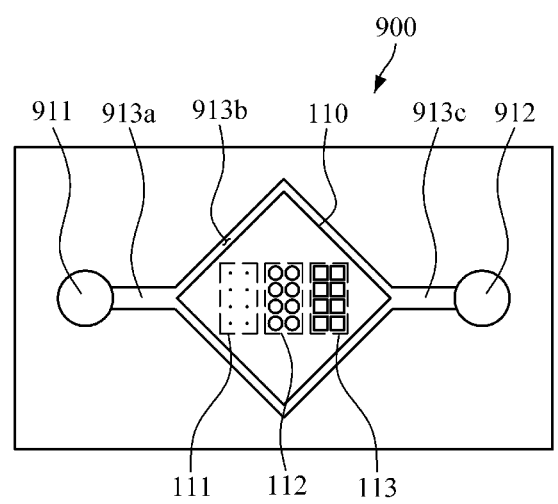
FIG. 9B is a top view of the apparatus for bio-particle detection of FIG. 9A.

FIG. 9A is an exploded perspective view of an apparatus for bio-particle detection according to an embodiment of the present disclosure. FIG. 9B is a top view of the apparatus for bio-particle detection of FIG. 9A.

FIG. 9A illustrates a first main body 910 having a sample solution inlet 911 and a sample solution outlet 912, a second main body 920 structurally connected to the first main body 910 to allow a fluid to flow, and the bio-particle detection chip 110 inserted between the first main body 910 and the second main body 920.

FIG. 9B illustrates the sample solution inlet 911, the sample solution outlet 912, the bio-particle detection chip 110, and channels 913a, 913b, and 913c formed between the first main body 910 and the second main body 920. In this case, the channels may include an injection path 913a, a main flow path 913b, and a discharge path 913c.

As illustrated in FIGS. 1 and 2, the bio-particle detection chip 110 may include the first through-hole group 111, the second through-hole group 112, and the third through-hole group 113. While FIGS. 9A and 9B illustrate an example in which the respective through-hole groups 111, 112, and 113 have different diameters, the through-hole groups may have the same diameter as illustrated in FIG. 1.

An apparatus 900 for bio-particle detection may include the optical signal detector 120, the processor 130, the electrical signal measurer 610, the sensor 710, and the like as illustrated in FIGS. 1 to 8.

Referring to FIGS. 9A and 9B, the sample solution injected into the sample solution inlet 911 may flow toward the bio-particle detection chip 110 through the injection path 913a, may flow through the main flow path 913b to be loaded into the bio-particle detection chip 110, and then may flow toward the sample solution outlet 912 through the discharge path 913c.

The sample solution may flow through the respective flow paths 913a, 913b, and 913c by capillary action, and/or may be loaded into the bio-particle detection chip 110.

In this case, the apparatus 900 for bio-particle detection may be formed in a structure for facilitating the capillary action, and/or may further include a material for facilitating the capillary action of the sample solution.

For example, the main flow path 913b may decrease in height, i.e., may be inclined from the injection path 913a toward the discharge path 913c, or the injection path 913a may have a width that gradually decreases in a flow direction of the sample solution.

In another example, the respective flow paths 913a, 913b, and 913c may be made of a hydrophilic material for facilitating the capillary action.

In yet another example, the apparatus 900 for bio-particle detection may include a porous medium inserted between the first main body 910 and the second main body 920. The porous medium may be made of a hydrophilic material, and may include a plurality of pores or a plurality of pin type microstructures.

Figure 10:
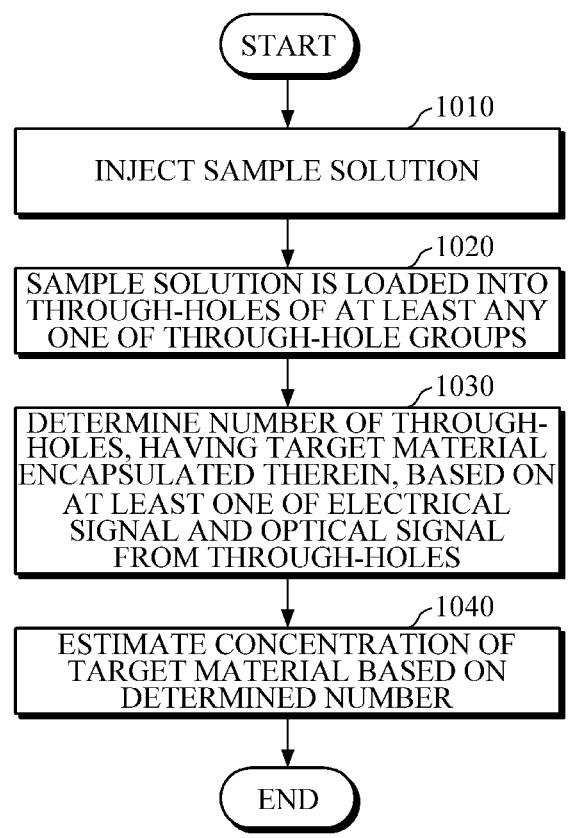
FIG. 10 is a flowchart illustrating a method of bio-particle detection according to an embodiment of the present disclosure.

FIG. 10 is a flowchart illustrating a method of bio-particle detection according to an embodiment of the present disclosure. The method of bio-particle detection of FIG. 10 may be performed by the apparatuses 100, 600, 700, 800, and 900 for bio-particle detection according to the embodiments of FIGS. 1, 6A 7, 8, and 9, which are described in detail above, and thus will be briefly described below in order to avoid redundancy.

First, the apparatus for bio-particle detection may inject a sample solution in operation 1010.

Then, the sample solution may be loaded into at least any one of the plurality of through-hole groups of the bio-particle detection chip in operation 1020. The sample solution may be loaded into the through-holes by capillary action.

The sample solution may contain a target material. In this case, examples of the target material may include ribonucleic acid (RNA) virus, deoxyribonucleic acid (DNA) virus, peptide nucleic acid (PNA) virus, and locked nucleic acid (LNA) virus (e.g., a duplex of one or more of ribonucleic acid (RNA) virus, deoxyribonucleic acid (DNA) virus, peptide nucleic acid (PNA) virus, and locked nucleic acid (LNA) virus), bacteria, pathogen, germ, virus, oligopeptide, protein, toxin, etc., but the target material is not limited thereto.

Before the sample solution is loaded into the through-holes, fluorescence, photothermal particles, quantum dot, and the like may be labeled on the target material by an antigen-antibody reaction.

In this case, the through-holes in the respective through-hole group may have the same diameter or different diameters. A detailed description thereof will be omitted.

Subsequently, the apparatus for bio-particle detection may determine the number of through-holes, having the target material encapsulated therein, based on at least one of the electrical signal and the optical signal in operation 1030.

For example, the apparatus for bio-particle detection may determine the number of through-holes, having the target material encapsulated therein, based on the optical signal, measured by the optical signal detector, in the bio-particle detection chip.

For example, the apparatus for bio-particle detection may determine the number of through-holes, having the target material encapsulated therein, based on fluorescence emanating from the target material, based on light transmittance at the through-holes, or based on a spectrum change in photonic crystal formed on the bio-particle detection chip. A detailed description thereof will be omitted.

In another example, based on a current change, an impedance change, and the like which are measured by the electrical signal measurer, the apparatus for bio-particle detection may determine the number of through-holes having the target material encapsulated therein.

For example, if the change in the impedance or current, which is measured at the electrodes, is greater than or equal to a threshold value, the apparatus for bio-particle detection may determine that the target material is encapsulated in the corresponding through hole. By contrast, if the change in impedance or current is not measured, or if the change value is less than the threshold value, the apparatus for bio-particle detection may determine that the target material is not encapsulated in the through-hole. In this manner, the apparatus for bio-particle detection may determine the number of through-holes having the target material encapsulated therein, compared to the number of the through-holes having the electrodes formed therein, thereby determining the number of through-holes in which the target material is encapsulated.

In yet another example, the apparatus for bio-particle detection may determine the number of through-holes, having the target material encapsulated therein, by combining the optical signal and the electrical signal.

Then, the apparatus for bio-particle detection may estimate the concentration of the target material based on the determined number in operation 1040. The apparatus for bio-particle detection may estimate the concentration of the target material for each through-hole group.

In this case, the apparatus for bio-particle detection may estimate the concentration of the target material by using a predetermined target material concentration estimation model based on Poisson distribution. A detailed description thereof will be omitted.

The present invention can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the present invention can be easily deduced by computer programmers of ordinary skill in the art, to which the present invention pertains.

Although various embodiments have been described, it will be understood by those skilled in the art that various changes and modifications can be made without changing technical ideas and essential features of the present disclosure. Thus, the above-described embodiments are illustrative in all aspects and are not intended to limit the present disclosure.

What is claimed is:

1. An apparatus for bio-particle detection, the apparatus comprising:
   a bio-particle detection chip comprising a substrate having a plurality of through-hole groups, each through-hole group of the plurality of through-hole groups including through-holes which pass through the substrate from a first surface of the substrate toward an second surface of the substrate opposite to the first surface, and which are configured to accommodate a sample solution loaded therein; and
   a processor configured to determine a number of through-holes, among the through holes of at least one through-hole group of the plurality of through-hole groups, having a target material encapsulated therein, based on at least one of an electrical signal and an optical signal corresponding to the through-holes of the at least one through-hole group, and to estimate a concentration of the target material based on the determined number;
   wherein the through-holes of each of the plurality of through-hole groups have at least one of diameters, volumes, shapes, or arrangement interval different than respective diameters, volumes, shapes, or arrangement interval of the through-holes of other through-hole groups of the plurality of through-hole groups.

2. The apparatus of claim 1, wherein the through-holes of each through-hole group of the plurality of through-hole groups have the diameters different than the diameters of the through-holes of other through-hole groups of the plurality of through-hole groups.

3. The apparatus of claim 2, wherein the diameters of the through-holes in the plurality of through-hole groups increase in a flow direction of the sample solution.

4. The apparatus of claim 1, further comprising an optical signal detector comprising:
   a light source configured to emit light to the bio-particle detection chip; and
   a detector configured to measure the optical signal scattered or reflected from the bio-particle detection chip.

5. The apparatus of claim 4, wherein the processor is further configured to determine the number of through-holes having the target material encapsulated therein, based on fluorescence measured by the optical signal detector, the fluorescence emanating from the target material by the light emitted to the loaded sample solution.

6. The apparatus of claim 4, wherein the processor is configured to determine the number of through-holes having the target material encapsulated therein, based on transmittance of the light through the through-holes measured by the detector.

7. The apparatus of claim 4, wherein the substrate comprises a structure formed with a metal nanostructure, and
   wherein the processor is further configured to identify a type of the target material based on plasmon resonance measured by the optical signal detector, the plasmon resonance occurring when the target material is attached to the structure formed with the metal nanostructure.

8. The apparatus of claim 7, wherein the structure formed with the metal nanostructure has a metasurface.

9. The apparatus of claim 4, wherein the through-holes in the at least one through-hole group of the plurality of through-hole groups are arranged in a photonic crystal, and wherein the processor is further configured to determine the number of through-holes having the target material encapsulated therein, based on a spectrum change in the photonic crystal measured by the detector.

10. The apparatus of claim 1, further comprising electrodes or transistors provided in at least a portion of the through-holes of each of the plurality of through-hole groups, and configured to measure an electrical signal corresponding to the at least the portion of the through-holes.

11. The apparatus of claim 10, wherein the processor is further configured to determine the number of through-holes having the target material encapsulated therein, based on at least one of an impedance change and a current change measured by the electrodes or the transistors.

12. The apparatus of claim 1, further comprising a temperature controller configured to control temperature of the through-holes to be at least one of a thermal dissolution temperature, a reverse transcription temperature, and a bio-particle amplification temperature.

13. The apparatus of claim 12, wherein in response to the target material being amplified based on temperature controlled by the temperature controller, the processor is further configured to determine the number of through-holes having the target material encapsulated therein, based on a result of the amplification.

14. The apparatus of claim 1, wherein the processor is further configured to estimate the concentration of the target material based on the determined number of through-holes having the target material encapsulated therein, and a predetermined target material concentration estimation model.

15. The apparatus of claim 1, wherein the substrate comprises a structure of multiple layers in which the plurality of through-hole groups are formed, and the sample solution flows through channels formed between the respective layers.

16. The apparatus of claim 1, wherein the processor is further configured to determine the number of through-holes having the target material encapsulated therein, based further on photothermal particles labeled on the target material before being loaded into the through-holes.

17. The apparatus of claim 16, further comprising an optical signal detector comprising:
  a light source configured to emit light onto the bio-particle detection chip; and
  a detector configured to measure the optical signal scattered or reflected from the bio-particle detection chip,
  wherein the processor is further configured to determine the number of through-holes having the target material encapsulated therein, based further on the optical signal from the photothermal particles.

18. The apparatus of claim 16, further comprising a temperature measuring sensor configured to measure temperature of the through-holes,
  wherein the processor is further configured to determine the number of through-holes having the target material encapsulated therein, based further on an amount of heat generated by a photothermal effect of the photothermal particles and measured by the temperature measuring sensor.

19. An apparatus for bio-particle detection, the apparatus comprising:
  a first main body comprising a sample solution inlet and a sample solution outlet;
  a second main body structurally connected to the first main body and configured to allow a fluid to flow;
  a bio-particle detection chip provided between the first main body and the second main body, the bio-particle detection chip comprising a substrate having a plurality of through-hole groups, each through-hole group of the plurality of through-hole groups including through-holes which pass through the substrate from a first surface of the substrate toward an second surface of the substrate opposite to the first surface, and which are configured to accommodate a sample solution loaded therein;
  channels provided between the first main body and the second main body, and configured to have a sample solution flow therethrough; and
  a processor configured to determine a number of through-holes, among the through holes of at least one through-hole group of the plurality of through-hole groups, having a target material encapsulated therein, based on at least one of an electrical signal and an optical signal corresponding to the through-holes of the at least one through-hole group, and estimate a concentration of the target material based on the determined number;
  wherein the through-holes of each through-hole group of the plurality of through-hole groups have at least one of diameters, volumes, shapes, or arrangement interval different than respective diameters, volumes, shapes, or arrangement interval of the through-holes of other through-hole groups of the plurality of through-hole groups.

20. The apparatus of claim 19, wherein the through-holes are configured to be loaded with the sample solution by capillary action.

* * * * *